(12) United States Patent
Tsuruta et al.

(10) Patent No.: US 9,013,193 B2
(45) Date of Patent: Apr. 21, 2015

(54) FLUID QUALITY SENSOR

(75) Inventors: Takashi Tsuruta, Osaka (JP); Kazuhiro Nishikawa, Osaka (JP); Koichi Kubota, Shiga (JP); Takuto Shibayama, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 427 days.

(21) Appl. No.: 13/466,759

(22) Filed: May 8, 2012

(65) Prior Publication Data

US 2012/0286810 A1 Nov. 15, 2012

(30) Foreign Application Priority Data

May 10, 2011 (JP) .................. 2011-104806

(51) Int. Cl.
*G01N 27/22* (2006.01)

(52) U.S. Cl.
CPC .................... *G01N 27/226* (2013.01)

(58) Field of Classification Search
CPC .................... G01N 27/221; G01N 27/226
USPC ............ 324/663, 690; 73/61.43–61.44, 61.61
See application file for complete search history.

(56) References Cited

U.S. PATENT DOCUMENTS

| | | | | |
|---|---|---|---|---|
| 3,006,189 A | * | 10/1961 | Warren et al. ............... 73/861.04 |
| 4,392,110 A | * | 7/1983 | El-Menshawy et al. ...... 324/453 |
| 4,543,191 A | * | 9/1985 | Stewart et al. ................. 210/746 |
| 4,559,493 A | * | 12/1985 | Goldberg et al. ............. 324/681 |
| 4,849,687 A | | 7/1989 | Sims et al. |
| 4,854,725 A | * | 8/1989 | Sims et al. ........................ 374/42 |
| 4,894,604 A | * | 1/1990 | Dowling et al. .............. 324/690 |
| 4,939,468 A | * | 7/1990 | Takeuchi ....................... 324/690 |
| 4,945,863 A | * | 8/1990 | Schmitz et al. ............... 123/1 A |
| 5,005,402 A | * | 4/1991 | Pischinger et al. ........... 324/663 |
| 5,017,879 A | * | 5/1991 | Lucas et al. ................... 324/663 |
| 5,089,783 A | * | 2/1992 | Kapsokavathis et al. ..... 324/672 |
| 5,103,184 A | * | 4/1992 | Kapsokavathis et al. ..... 324/672 |
| 5,124,654 A | * | 6/1992 | Scheid ........................... 324/658 |
| 5,124,655 A | * | 6/1992 | Takeuchi et al. .............. 324/690 |
| 5,134,381 A | * | 7/1992 | Schmitz et al. ............... 324/685 |
| 5,205,151 A | * | 4/1993 | Shimamura et al. ........... 73/1.02 |
| 5,216,409 A | * | 6/1993 | Ament et al. ................. 340/438 |
| 5,231,358 A | * | 7/1993 | Kapsokavathis et al. ..... 324/672 |
| 5,343,758 A | * | 9/1994 | Ingrain et al. .............. 73/861.02 |
| 5,416,425 A | * | 5/1995 | Mouaici ........................ 324/690 |
| 5,717,339 A | * | 2/1998 | Murphy et al. ............... 324/693 |

(Continued)

FOREIGN PATENT DOCUMENTS

| | | |
|---|---|---|
| JP | 62-191748 | 8/1987 |
| JP | 64-033059 U | 3/1989 |

(Continued)

*Primary Examiner* — Huy Q Phan
*Assistant Examiner* — James Split
(74) *Attorney, Agent, or Firm* — Hamre, Schumann, Mueller & Larson, P.C.

(57) ABSTRACT

An object of the present invention is to accurately detect concentrations of mixtures in a fluid. An internal electrode 23 is disposed on the inner side of an external electrode 22 coaxially with the external electrode 22, and a plurality of points in the length direction of the internal electrode 23 are supported by a casing 21 via supporting members 28*a* and 28*b*. The state of a fluid S passing through a passage 26 between the external electrode 22 and the internal electrode 23 is detected based on electrostatic capacitance between the external electrode 22 and the internal electrode 23.

11 Claims, 8 Drawing Sheets

(56) References Cited

U.S. PATENT DOCUMENTS

| | | | |
|---|---|---|---|
| 5,861,755 A * | 1/1999 | Moerk et al. | 324/663 |
| 6,057,693 A * | 5/2000 | Murphy et al. | 324/663 |
| 6,586,949 B1 * | 7/2003 | Sargent et al. | 324/690 |
| 6,586,950 B1 * | 7/2003 | Sargent et al. | 324/690 |
| 6,885,199 B2 * | 4/2005 | Desmier et al. | 324/663 |
| 7,030,629 B1 * | 4/2006 | Stahlmann et al. | 324/663 |
| 7,380,468 B2 * | 6/2008 | Beaulieu et al. | 73/861.12 |
| 7,466,147 B2 * | 12/2008 | Stahlmann | 324/663 |
| 8,072,229 B2 * | 12/2011 | Nakamura et al. | 324/663 |
| 8,264,241 B2 * | 9/2012 | Slezak et al. | 324/658 |
| 2009/0153149 A1 * | 6/2009 | Hernandez et al. | 324/663 |

FOREIGN PATENT DOCUMENTS

| | | |
|---|---|---|
| JP | 02-213760 | 8/1990 |
| JP | 07-092130 | 4/1995 |
| JP | 2639753 B | 5/1997 |
| WO | WO 2007/019577 | 2/2007 |

* cited by examiner

F I G. 1 1   PRIOR ART
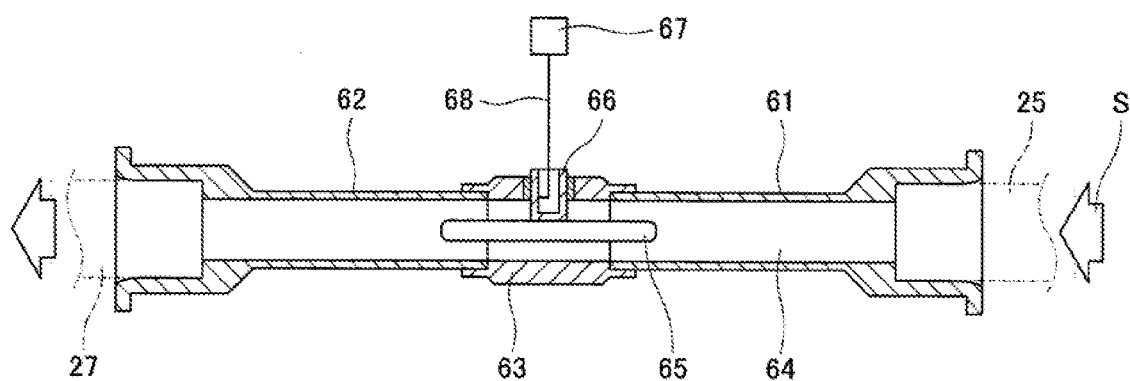
F I G. 1 2   PRIOR ART
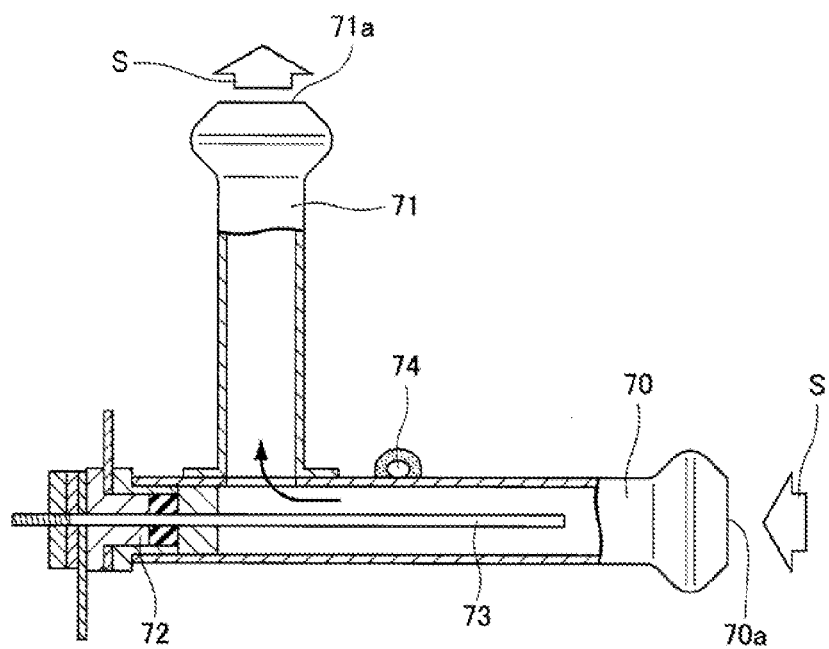

FLUID QUALITY SENSOR

FIELD OF THE INVENTION

The present invention relates to a fluid quality sensor for detecting the concentration of a fluid by a capacitive sensing method.

BACKGROUND OF THE INVENTION

FIG. 11 shows a fluid quality sensor of WO2007/019577. In order that a fluid S flowing from an upstream fluid pipe 25 toward a downstream fluid pipe 27 may be detected based on electrostatic capacitance and temperature, a pipe 61 connected to the fluid pipe 25, a pipe 62 connected to the fluid pipe 27, and an intermediate pipe 63 interposed between the pipes 61 and 62 form a fluid path 64. An internal electrode 65 is disposed on the fluid path 64 inside the immediate pipe 63 via a supporting member 66. The intermediate pipe 63 is an external electrode, and the internal electrode 65 is electrically insulated from the immediate pipe 63 by the supporting member 66. A temperature sensor 67 indirectly detects the temperature of the internal electrode 65 with a detector 68 thermally connected to the supporting member 66.

Thus, based on a capacitance value between the intermediate pipe 63 and the internal electrode 65 and a temperature detected by the temperature sensor 67, the state such as the concentration of the fluid is detected.

Further, FIG. 12 shows a fluid quality sensor of Japanese Patent No. 2639753.

Pipes 70 and 71 are joined to each other in a substantially T-shape. A fluid S flows in from an inlet 70a on one end of the pipe 70 and flows out from an outlet 71a on one end of the pipe 71. The other end of the pipe 70 is closed by an electrode inserting member 72. An internal electrode 73 is inserted from the other end toward the one end of the pipe 70. Reference numeral 74 denotes a temperature sensor attached to the outer peripheral surface of the pipe 70.

Thus, based on a capacitance value between the pipe 70 and the internal electrode 73 and a temperature detected by the temperature sensor 74, the state such as the concentration of the fluid S is detected.

DISCLOSURE OF THE INVENTION

However, in the first related art example of FIG. 11, the rod-shaped internal electrode 65 in the fluid path 64 is held at only one point by the supporting member 66, and thus excessive stress is applied on the supporting member 66 according to the flow rate and the viscosity of the fluid S. It is highly likely that the excessive stress applied on the supporting member 66 causes the internal electrode 65 to vibrate or be displaced. In order to avoid the problem, in general, the thickness of the supporting member 66 or a distance between electrodes is increased. However, the increased distance between electrodes inevitably reduces the detection accuracy. Further, the cross-sectional area of the fluid path becomes non-uniform and the flow of the fluid S is disturbed, and thus the detection accuracy becomes unstable in sensing the fluid S with time and small changes in the properties of the fluid S are hardly noticed.

The present invention has been devised to solve the problem. An object of the present invention is to provide a fluid quality sensor capable of detecting the fluid S with high accuracy over a long time despite the flow rate and the viscosity of the fluid S.

A fluid quality sensor for measuring mixture fluid includes: a tubular external electrode disposed on a first passage on an inner side of a tubular casing; an internal electrode having supporting members at both end connected to the casing so as to be disposed on an inner side of the external electrode coaxially with the external electrode, a intake part which are attached to one end of the casing, and have a second passage communicated with the first passage formed between an inner circumference of the external electrode and an outer periphery of the internal electrode; and a outlet part which are attached to another end of the casing, and have a third passage communicated with the first passage, wherein concentration of a fluid passing through the first passage is detected based on electrostatic capacitance between the external electrode and the internal electrode.

Preferably, both ends of the internal electrode are extended along the second and third passages respectively, and cross-sectional areas of the second passage and the third passage are equal to that of the first passage.

Preferably, the both ends of the internal electrode are cone-shaped, and the second and third passages of the intake and outlet parts are tapered along the cone-shapes of the both ends of the internal electrode respectively. Angles of the cone-shapes of the both ends of the internal electrode are 10° to 60°.

Preferably, at least two points in a outer surface of the internal electrode are attached to the casing by the supporting members.

Preferably, first members are attached to both ends of the external electrode, the first members having holes in centers of the first members through which the internal electrode passes and being made of electrical insulators, second members are attached onto outer sides of the first members, the second members having holes in centers of the second members through which the internal electrode passes and being made of electrical conductors, and inner surfaces of the second members and an outer surface of the internal electrode are connected by the supporting members, the first members with the external electrode attached thereto and the second members with the internal electrode attached thereto are inserted into the first passage, and are positioned in a diameter direction of the casing, the intake and outlet parts are attached to the both ends of the casing respectively, so that the external electrode, the internal electrode, the first members, and the second members are located, and the external electrode and the first members, the first members and the second members, and the second members and the adapters are sealed with sealing materials. A temperature sensor is connected to the external electrode.

According to the present invention, the plurality of points of the internal electrode in the direction of the passage are supported by the casing via the supporting members such that the internal electrode is held on the inner side of the external electrode coaxially with the external electrode. Thus, the position of the internal electrode can be precisely retained and high detection accuracy can be secured over a long time.

BRIEF DESCRIPTION OF THE DRAWINGS

FIG. 11 is a cross-sectional view of a fluid quality sensor of the related art described in WO2007/019577; and FIG. 12 is a cross-sectional view showing a fluid quality sensor of the related art described in Japanese Patent No. 2639753.

DESCRIPTION OF THE EMBODIMENTS

Figure 1:
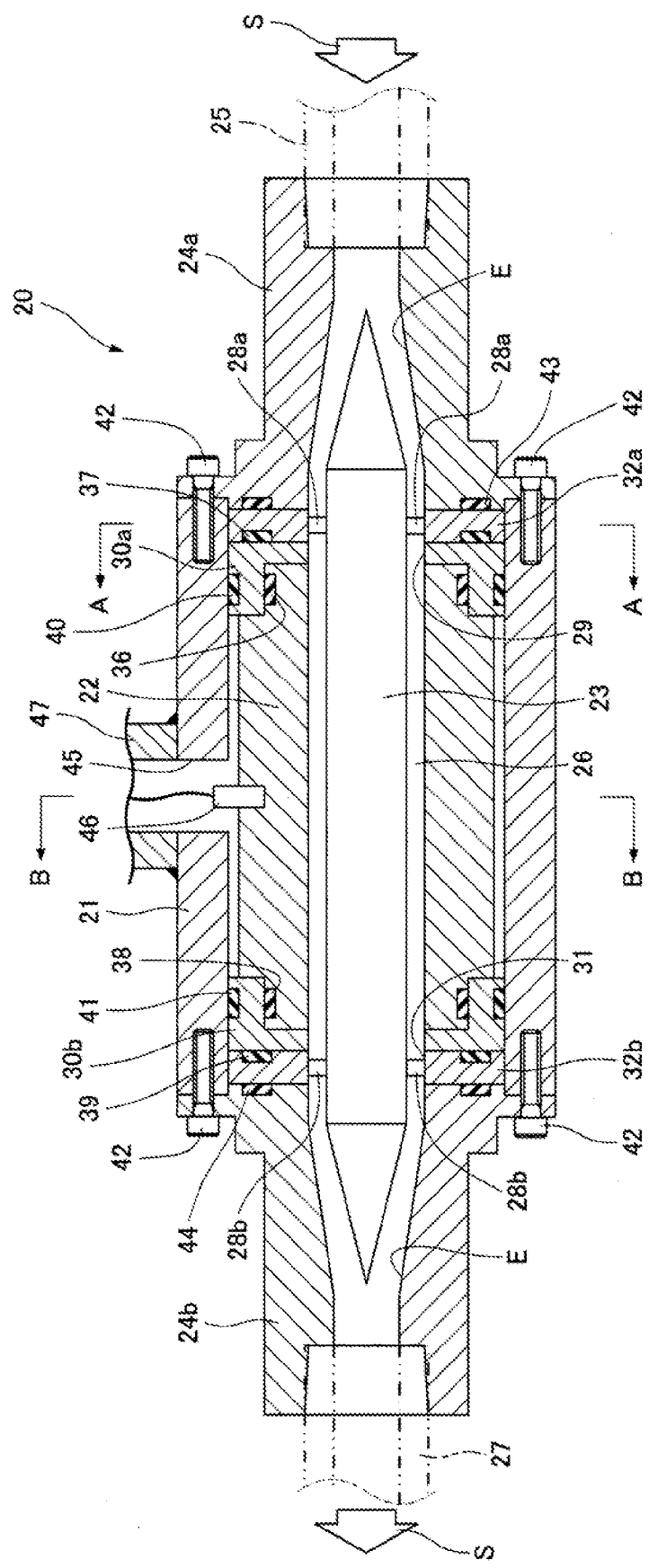
FIG. 1 is a schematic cross-sectional view showing a fluid quality sensor according to a first embodiment of the present invention.
Figure 2:
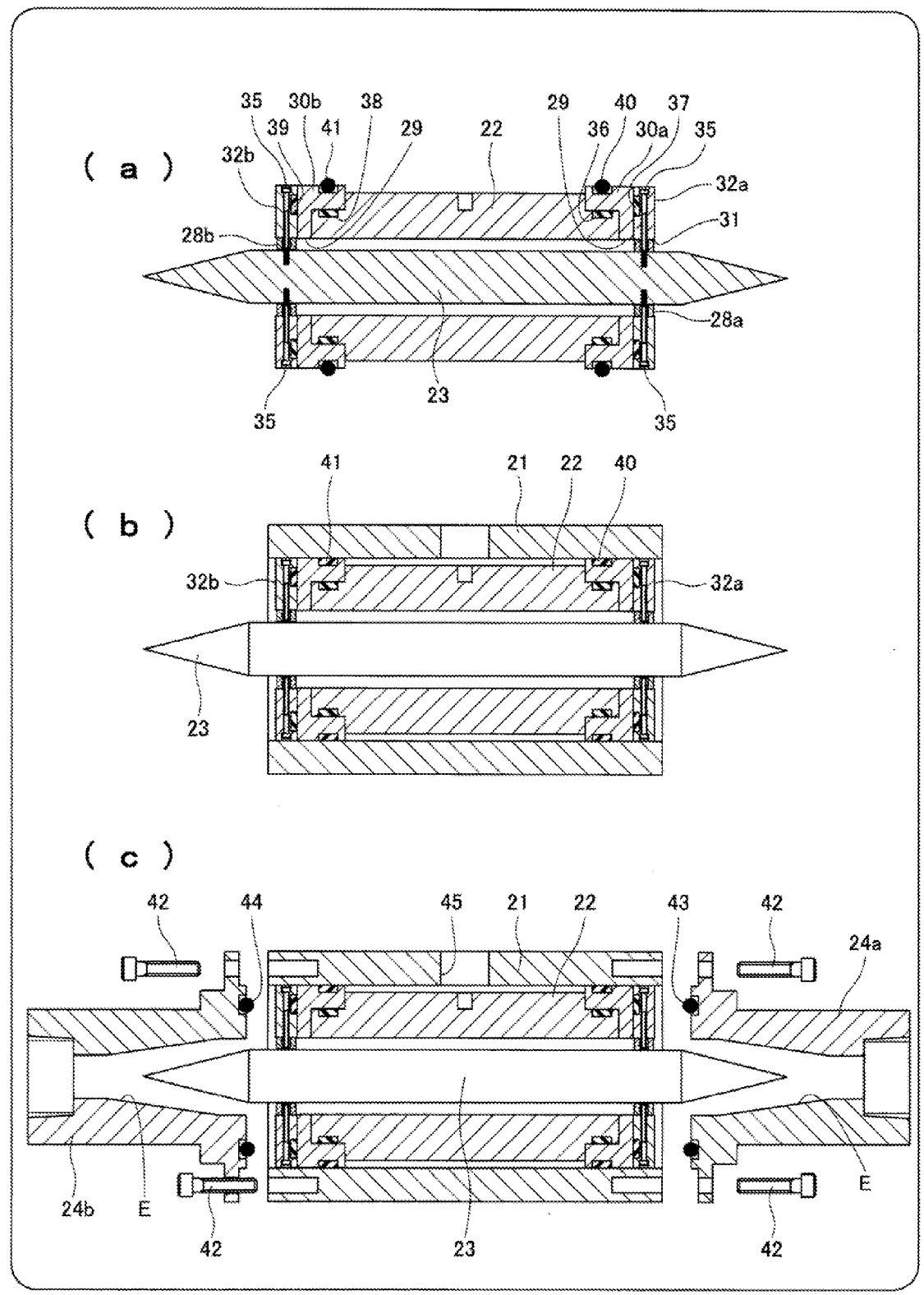
FIG. 2 is a fabrication process drawing according to the first embodiment.

The following will describe embodiments of the present invention in accordance with FIGS. 1 to 10.
(First Embodiment)
FIGS. 1 to 5 show a fluid quality sensor 20 according to a first embodiment.

The fluid quality sensor 20 includes: a tubular casing 21; a tubular external electrode 22 fixed to the inner side of the casing 21; an internal electrode 23 disposed on the inner side of the external electrode 22 coaxially with the external electrode 22; and adapters 24a and 24b attached to ends of the casing 21. A fluid S flows into the fluid quality sensor 20 from a fluid pipe 25 connected to the adapter 24a.

The fluid S having flowed into the fluid quality sensor 20 passes through a detection passage 26 formed between the inner circumference of the external electrode 22 and the outer periphery of the internal electrode 23 and flows out of a fluid pipe 27 connected to the adapter 24b via the adapter 24b.

The internal electrode 23 having two cone-shaped ends is supported by the casing 21 via supporting members 28a and 28b at multiple points, in this embodiment, at two points in the direction of the detection passage 26. The internal electrode 23 is larger in length than the external electrode 22, and the supporting members 28a and 28b are positioned outside the opposed part of the external electrode 22 and the internal electrode 23.

The configuration will be specifically described based on a fabrication process.

As shown in FIG. 2(a), first members 30a and 30b, which have holes 29 in the centers thereof and are made of electrical insulators, are attached to two ends of the external electrode 22.

Onto the outer sides of the first members 30a and 30b, second members 32a and 32b are attached which have holes 31 in the centers thereof and are made of electric conductors, and the inner circumferential surfaces of the second members 32a and 32b and the outer peripheral surface of the internal electrode 23 are connected by the supporting members 28a and 28b which are made of electric conductors.

The inner circumference of the external electrode 22, the first member 30a, the second member 32a, and an internal passage E of the adapter 24a are flush with each other. Further, the inner circumference of the external electrode 22, the first member 30b, the second member 32b, and an internal passage E of the adapter 24b are flush with each other.

Figure 3:
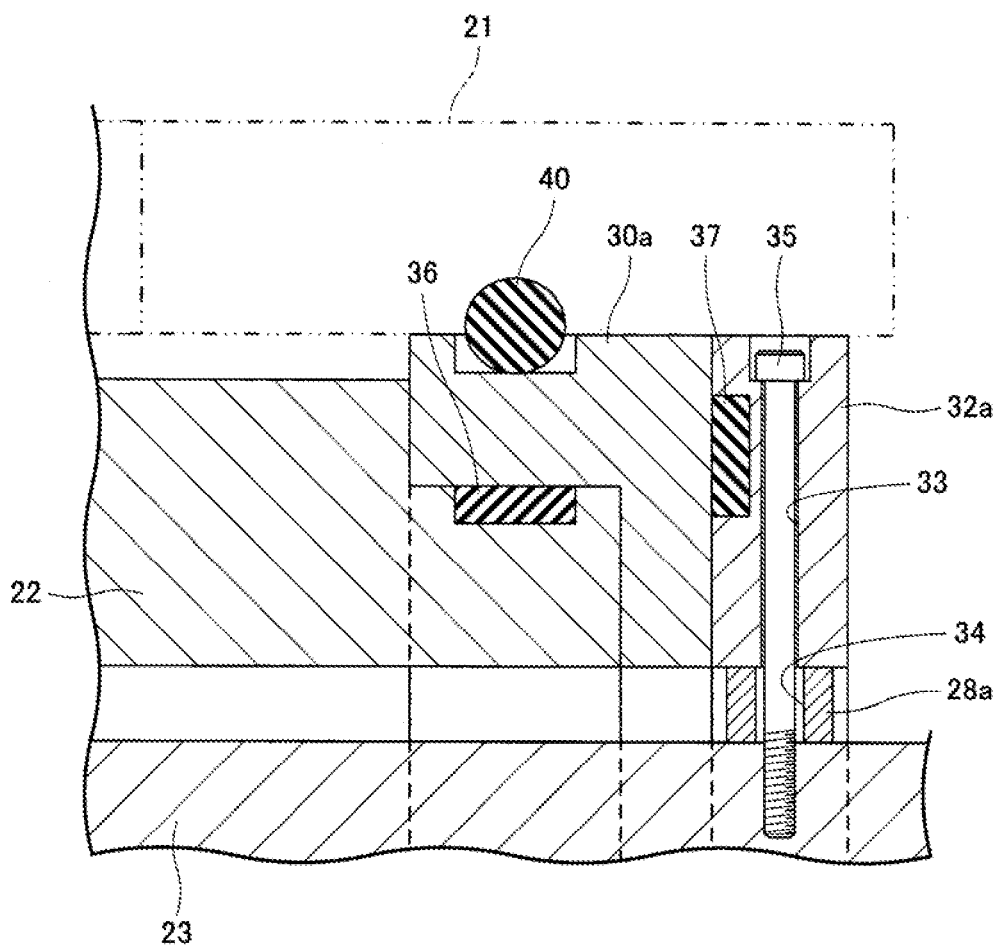
FIG. 3 is an enlarged cross-sectional view showing the main part of FIG. 2.

Specifically, as shown in FIG. 3, a bolt 35 is inserted into a through hole 33 formed in the second member 32a and a center hole 34 of the supporting member 28a, and the tip of the bolt 35 is screwed and tightened into the internal electrode 23. Bolting is performed also on the side of the second member 32b.

A contact surface between the outer periphery of the end of the external electrode 22 and the inner circumferential surface of the first member 30a is sealed with an O-ring 36. A contact surface between the first member 30a and the second member 32a is sealed with an O-ring 37. A contact surface between the outer periphery of the end of the external electrode 22 and the inner circumferential surface of the first member 30b is sealed with an O-ring 38. A contact surface between the first member 30b and the second member 32b is sealed with an O-ring 39.

Next, as shown in FIG. 2(b), the first members 30a and 30b with the external electrode 22 and the second members 32a and 32b with the internal electrode 23 are inserted into the passage on the inner side of the casing 21, and are positioned in the diameter direction of the passage on the inner side of the casing 21. The outer peripheral surface of the first member 30a and the inner circumferential surface of the casing 21 are sealed with an O-ring 40, and the outer peripheral surface of the first member 30b and the inner circumferential surface of the casing 21 are sealed with an O-ring 41.

In FIG. 2(c), the adapters 24a and 24b are attached to the ends of the casing 21 with bolts 42. A contact surface between the second member 32a and the adapter 24a is sealed with an O-ring 43, and a contact surface between the second member 32b and the adapter 24b is sealed with an O-ring 44. The internal passages E of the adapters 24a and 24b are tapered along the cone-shaped ends of the internal electrode 23.

After the above-described fabrication process, a temperature sensor 46 is thermally connected to the outer peripheral surface of the external electrode 22 exposed from a hole 45 of the casing 21. As shown in FIG. 1, a cylinder 47 is attached to the outer peripheral surface of the casing 21 so as to be communicated with the hole 45.

Figure 4:
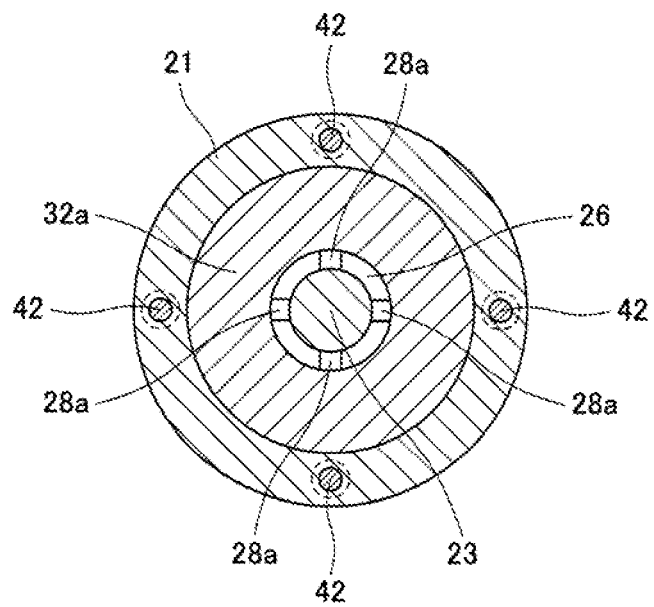
FIG. 4 is a cross-sectional view taken along the arrows A-A of FIG. 1.
Figure 5:
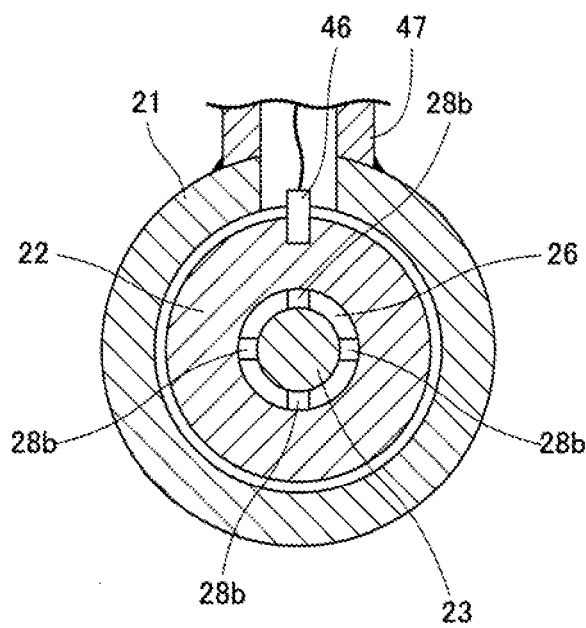
FIG. 5 is a cross-sectional view taken along the arrows B-B of FIG. 1.

FIG. 4 is a partial cross-sectional view taken along the arrows A-A of FIG. 1. FIG. 5 is a partial cross-sectional view taken along the arrows B-B of FIG. 1.

In this configuration, a capacitance value between the external electrode 22 and the internal electrode 23 is measured to determine the chemical concentration of the fluid S. At this point, the dielectric constant varies depending on the temperature of the fluid S in addition to the concentration. Thus, the temperature sensor 64 is provided. For the measurement of the capacitance value between the external electrode 22 and the internal electrode 23 and the temperature sensor 46, a known technique is used to implement the measurement.

The two ends of the internal electrode 23 are cone-shaped and the inner circumferential surfaces of the adapters 24a and 24b are tapered along the ends of the internal electrode 23 such that the cross-sectional areas of flow paths between the internal electrode 23 and the adapter 24a and between the internal electrode 23 and the adapter 24b are substantially equal to the cross-sectional area of a flow path between the internal electrode 23 and the external electrode 22 except for the locations of the supporting members 28a and 28b, in the cross-sectional area of a flow path from the fluid pipe 25 through the fluid quality sensor 20 out of the fluid pipe 27. Thus, the flow of the fluid S can be made a laminar flow passing through the detection passage 26.

When the maximum angle of the cone-shaped portion of the internal electrode 23 exceeds 60°, the resistance of the fluid increases and a force acts on the sensor, thereby impeding stable measurement. When the minimum angle thereof is smaller than 10°, the sensor is reduced in thickness, and is thus distorted or bent, thereby preventing measurement. Consequently, the angle of the cone-shaped portion is preferably within a range of 10° to 60°. Further, when the maximum angle is reduced from 60° to 45°, the resistance of the fluid decreases, most of the fluid to be detected becomes a laminar flow, the measurement is stabilized, and the measurement accuracy is increased. When the minimum angle is increased from 10° to 20°, the rigidity of the sensor increases, the cone-shaped portion becomes smaller in length in the axial direction, and the total length of the sensor is reduced, so that the measurement accuracy is increased. Consequently, the angle of the cone-shaped portion is more preferably within a range of 20° to 45°.

In the drawings, the angles of the cone-shaped portions of the internal electrode 23 are set at 25° such that the cross-sectional area of the detection passage 26 becomes constant.

If the cone shape on the downstream end of the internal electrode 23 is eliminated, the fluid swirls in the vicinity of the downstream side of the internal electrode 23, and the flow therearound is disturbed. As shown in FIG. 1, when the detection passage 26 of the fluid quality sensor 20 is straight, the two ends of the internal electrode 23 are preferably cone-shaped.

The supporting members 28a and 28b are column-shaped to reduce the flow resistance of the fluid S as much as possible and preferably have a diameter of about 1 mm to 3 mm. The range of detection of the fluid quality sensor 20 is determined according to the opposed length of the external electrode 22 and the internal electrode 23. The external electrode 22 is provided on the outer side of the internal electrode 23 so as to be opposed to the internal electrode 23 between the supporting members 28a and 28b. Thus, despite the provision of the supporting members 28a and 28b, the range of detection forms a cylindrical shape having a uniform cross-sectional area.

In this configuration, the two ends of the internal electrode 23 are supported by the casing 21 via the supporting members 28a and 28b, the position of the internal electrode 23 is precisely held, the two ends of the internal electrode 23 are cone-shaped to uniform the cross-sectional area of the fluid passage, and the fluid to be detected is made as close to a laminar flow as possible, so that higher detection accuracy can be secured.

If the internal electrode 23 is column-shaped and is supported by the casing 21 on only one side, the internal electrode easily bends in the diameter direction from the base of a supporting member 66 in FIG. 11 and the end on the fluid passage side of an electrode inserting portion 72 in FIG. 12, and a distance between the electrodes is reduced, so that the measurement accuracy is varied. Such deflection gradually increases due to the pressure of the fluid, thereby gradually varying the measurement accuracy. For example, when the distance between the electrodes is 5 mm and an amount of deflection (misalignment) of 0.5 mm is generated, the detection accuracy is varied by about 10%. Further, this phenomenon occurs in an enclosed region and thus tends to be found in a delayed fashion. When the internal electrode happens to contact the external electrode, detection becomes impossible.

In the above-described embodiment, the internal electrode 23 is screwed and fixed on two sides in four directions via the column-shaped supporting members 28a and 28b as shown in FIGS. 4 and 5, but may be screwed and fixed in two or three directions depending on the intended use.

Example 1

Figure 6:
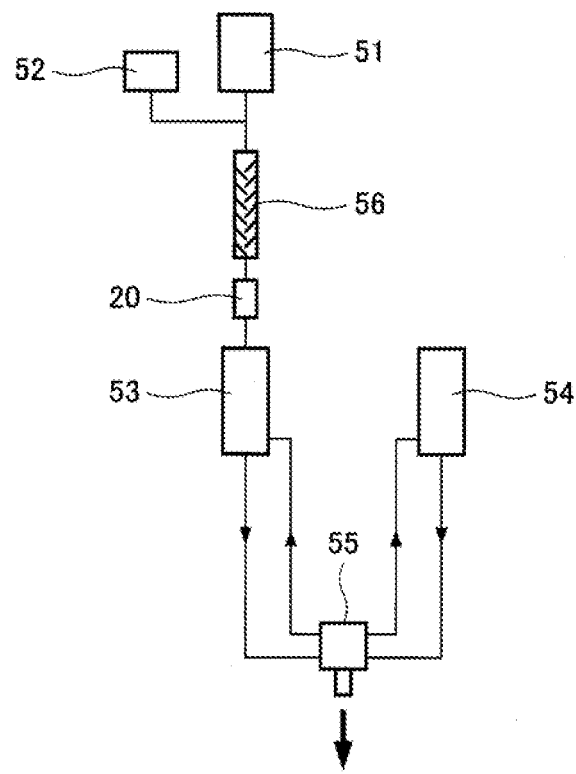
FIG. 6 is a configuration diagram showing urethane foaming equipment in a first example.

FIG. 6 shows a specific example of the fluid quality sensor 20 placed in the material supply piping of urethane foaming equipment for refrigerator insulation.

The equipment includes: circulating material supply piping containing a premix material 53 having a second material 52 (cyclopentane) acting as a foaming agent mixed in a first material 51 (polyol component); circulating material supply piping containing a third material 54 (isocyanate component); and a mixing head 55 which mixes and discharges the materials. The equipment is production equipment which injects an urethane raw material into a thermally-insulated housing of a refrigerator or the like.

A liquid-liquid mixer 56 typified by a static mixer is used for mixing the first material 51 and the second material 52. Since the second material acting as a foaming agent is cyclopentane in the production equipment, the fluid quality sensor 20 of the production equipment conforms to the specification of intrinsic safety explosion-proof construction.

Since the second material 52 is a foaming agent, the mixture ratio is significantly associated with the fluidity after mixing and discharging. The mixed materials progressively react and are cured with time immediately after the mixed materials are injected to the thermally-insulted housing of a refrigerator or the like. However, an extremely insufficient amount of the foaming agent reduces the expansion ratio, and thus the mixed materials do not spread into every corner of the thermally-insulated housing, thereby causing insufficient filling. As a result, the rigidity of the housing is reduced in addition to a loss of the thermal insulation performance. Further, an excessive amount of the foaming agent causes excessive filling, thereby resulting in inferior quality such as a deformed housing or urethane leakage. Thus, the concentration control of the second material 52 acting as a foaming agent becomes important.

In the first embodiment, the fluid quality sensor 20 is provided on the downstream material supply piping in which the first material 51 and the second material 52 are mixed. Materials of three levels (X−1 wt %/X wt %/X+1 wt %) obtained by varying a mixture fraction X of the second material 52 to the first material 51 in increments of 1 wt % were used, and capacitance values were measured at three levels of material temperatures (21° C./23° C./25° C.) in consideration of variations in capacitance values according to temperatures.

In the present example, the dielectric constant of the first material 51 is about 11.1, and the dielectric constant of the second material 52 is about 2.6. Since the material having a low dielectric constant is mixed in the material having a high dielectric constant, it can be predicted that the capacitance values are reduced as the mixture fraction X increases.

The fluid quality sensor 20 has a detection range in a cylindrical shape having a uniform cross-section with a distance between the electrodes of 2.8 mm and a detection length of 100 mm. After the application of an oscillation frequency of 200 kHz from an oscillator, the frequency is converted to a DC voltage and is outputted by a frequency-voltage converter circuit. The outputted voltage is detected as the DC voltage in a range of 0 V to 10 V, and is controlled to change by 10 V relative to a capacitance variation of 10 pF.

Figure 7:
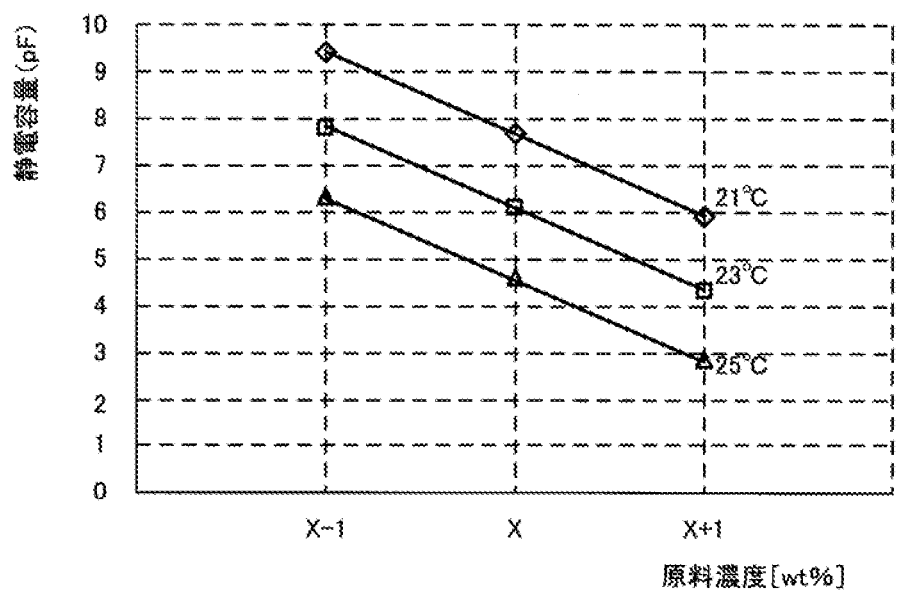
FIG. 7 is an input/output characteristic diagram of measurement results of electrostatic capacitance in the first example.

FIG. 7 shows results of measuring electrostatic capacitance.

It can be seen that the capacitance value increases as the material temperature decreases and the capacitance value is easily influenced by the material temperature. Every material at every mixture fraction shows high linearity. Thus, it can be seen that the temperature can be easily compensated by controlling the temperature of the fluid to be detected to effectively detect the material concentration. Hence, the foaming qualities of polyurethane foam insulation and an insulation box using the polyurethane foam insulation can be improved.

The detection range with the distance between the electrodes of 2.8 mm and the detection length of 100 mm may be set to have proper dimensions according to the dielectric constant of the fluid S.

Example 2

Figure 8:
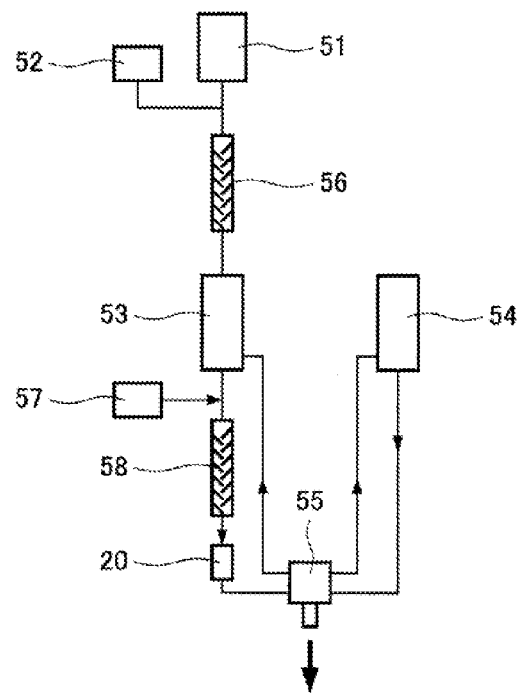
FIG. 8 is a configuration diagram showing urethane foaming equipment in a second example.

FIG. 8 is different from FIG. 6 in that a foaming agent 57 (carbon dioxide) having a boiling point of 0° C. or lower at substantially atmospheric pressure is mixed on the upstream side of the mixing head 55. The mixed path is disclosed by Japanese Patent Application Laid-Open Publication No. 2010-1038239. The fluid quality sensor 20 is interposed on the subsequent stage of a liquid-liquid mixer 58. Others are the same as those in FIG. 6.

The newly-mixed foaming agent 57 evaporates at substantially atmospheric pressure, and thus generates air bubbles in the premix material 53. Hence, the liquid-liquid mixer 58, and so on are desirably used in a high-pressure ambience of about 8 MPa to 13 MPa. The premix material 53 and the foaming agent 57 are mixed by the liquid-liquid mixer 58, are then mixed with the third material 54 by the mixing head 55, and are discharged out of the system. Since the discharged materials contain the foaming agent 57 which easily evaporates at substantially atmospheric pressure, foaming starts immediately after discharging. The mixture fraction of the foaming agent 57 to the premix material 53 frequently used is about 0.1 wt % to 1 wt %. For this reason, similarly to the first embodiment, the detection and control of mixture distribution in the mixed amount and discharge time of the foaming agent 57 significantly affect the foaming quality. The foaming agent 57 is mixed according to the discharge timing. Thus, the foaming agent 57 does not return to the circulating material supply piping.

The mixed amount of the foaming agent 57 has been detected by a known flowmeter typified by a Coriolis flowmeter. The Coriolis flowmeter has a U-shaped flow tube in which the fluid to be detected flows. The Coriolis force acts in opposite directions between two legs (of the tube), so that the tube is distorted. The torsion angle of the tube is measured to determine the flow rate of the fluid. However, the Coriolis flowmeter has the U-shaped flow tube in which a loss of pressure and vibrations disadvantageously affect the provision of the fluid quality sensor on the equipment piping. The mixed amount of the foaming agent 57 targeted by the present invention is small, about 0.1 wt % to 1 wt % to the premix material 53. In using the Coriolis flowmeter, the flow tube has to be reduced in thickness to increase the sensitivity, and due to the loss of pressure and vibrations, the foaming agent 57 cannot be precisely detected.

In the second example, the mixture fraction is significantly different from that in the first example, and thus the electrode capacitance specific to the sensor has to be optimized. The detection range of the fluid quality sensor 20 is changed to a detection range of a distance between the electrodes of 1.65 mm/a detection length of 135 mm.

Figure 9:
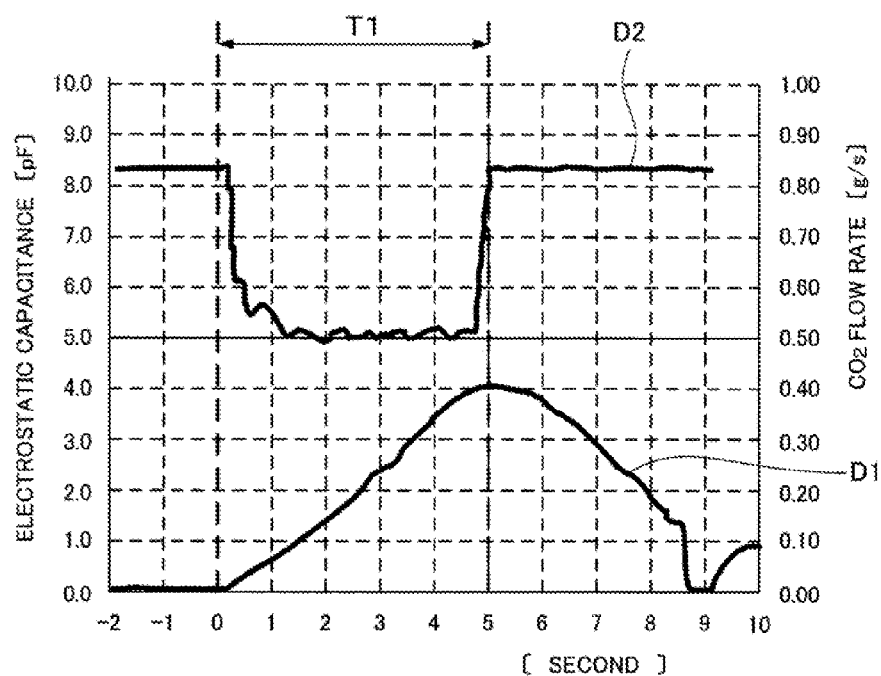
FIG. 9 is an input/output characteristic diagram of measurement results of electrostatic capacitance in the second example.

FIG. 9 shows the results of measuring electrostatic capacitance in the second example.

A mountain-shaped waveform D1 shows the results of measuring the flow rate of $CO_2$ by means of the Coriolis flowmeter, and a concave waveform D2 shows the results of measuring the flow rate of $CO_2$ by means of the fluid quality sensor 20. In either case, an actual discharge time T1 is five seconds, but in the measurement by means of the Coriolis flowmeter, poor responsiveness is exhibited before the peak of the flow rate and the measurement continues beyond the actual discharge time. Thus, the actual mixed amount of the foaming agent 57 cannot be determined. Meanwhile, in the measurement by means of the fluid quality sensor 20, the response time is about one second before the peak of electrostatic capacitance, and the response time is within 0.3 seconds before recovery to the initial value at the end of discharging. Thus, the measurement can be achieved at higher accuracy. Further, when the conditions of the waveforms can be more specifically detected, the mixture distribution can be more precisely detected.

(Second Embodiment)

Figure 10:
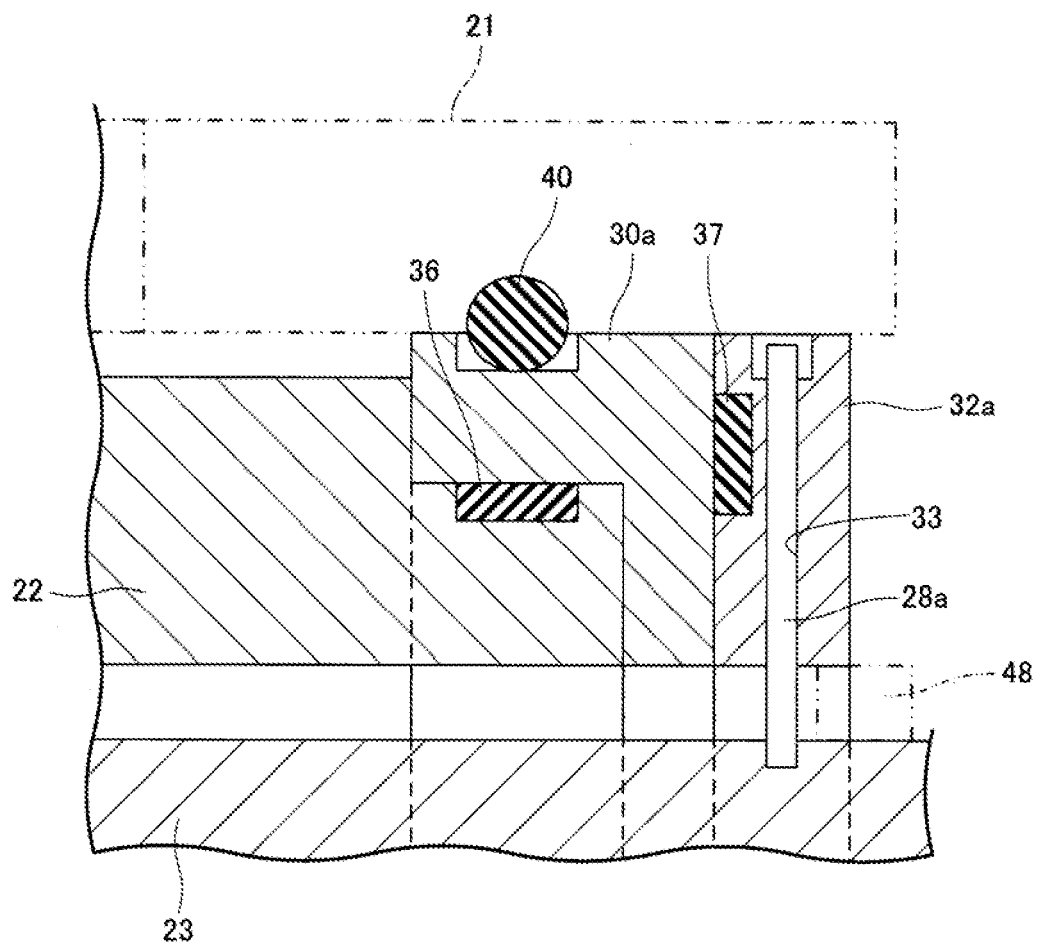
FIG. 10 is an enlarged cross-sectional view showing a main part according to a second embodiment of the present invention.

FIG. 10 shows a fluid quality sensor 20 according to a second embodiment of the present invention.

In the first embodiment, the bolts 35 are tightened between the internal electrode 23 and the second members 32a and 32b with the supporting members 28a and 28b interposed therebetween. The second embodiment is different from the first embodiment only in that welding and fixing are performed between an internal electrode 23 and second members 32a and 32b with supporting members 28a and 28b (not shown) interposed therebetween.

In the process, the supporting member 28a is inserted into a through hole 33 of the second member 32a to cause the leading end of the supporting member 28a to contact the internal electrode 23. At this point, a gap forming jig 48 having electrical insulation is interposed between the second member 32a and the internal electrode 23 to keep a gap between the second member 32a and the internal electrode 23 at a specified value. With the gap between the second member 32a and the internal electrode 23 kept at the specified value, electricity is conducted between the internal electrode 23 and the supporting member 28a while the supporting member 28a is pressed against the internal electrode 23, so that the leading end of the supporting member 28a is welded to the internal electrode 23.

Next, electricity is conducted between the supporting member 28a and the second member 32a to weld the supporting member 28a to the second member 32a.

Similarly, welding is performed between the supporting member 28b (not shown) and the internal electrode 23 and between the supporting member 28b (not shown) and the second member 32b (not shown), and thereafter, all the gap forming jigs 48 are removed.

Thus, welding and fixing are performed between the internal electrode 23 and the second members 32a and 32b (not shown) with the supporting members 28a and 28b (not shown) interposed therebetween, so that areas occupied by the supporting members 32a and 32b (not shown) in a detection passage 26 can be reduced as compared with in the bolt fixation of the first embodiment, thereby improving the accuracy of detecting the flow rate.

The fluid quality sensor of the present invention can accurately detect concentrations of mixtures in the fluid to be detected, thereby improving the qualities of components and products manufactured using the fluid to be detected.

What is claimed is:

1. A fluid quality sensor for measuring mixture fluid comprising:
   a tubular casing having a first end and a second end and extending in an axial direction from the first end to the second end;
   a tubular external electrode disposed in an interior space defined by the tubular casing;
   an internal electrode disposed in an interior space defined by the external electrode, the internal electrode being positioned apart from and coaxially with the external electrode, a first passage being formed between an inner surface of the external electrode and an outer surface of the internal electrode;

a pair of first members engaged with the external electrode in the axial direction, each of the first members including an electrical insulator;

a pair of second members engaged with the pair of the first members, respectively, in the axial direction, each of the second members including at least one hole extending in a radial direction through the respective second member; each of the second members being engaged with an inner surface of the tubular casing in a radial direction, thereby preventing the second members from moving in the radial direction relative to the tubular casing, each of the second members including an electrical conductor;

at least one supporting member connecting a surface of the at least one hole defined in each of the second members and the outer surface of the internal electrode, the at least one support member including an electrical conductor;

an annular intake part engaged with the first end of the tubular casing in the axial direction, a second passage being formed in the annular intake part; and an annular outlet part engaged with the second end of the tubular casing in the axial direction, a third passage being formed in the annular outlet part, wherein concentration of a fluid passing from the second passage through the first passage to the third passage is detected based on electrostatic capacitance between the external electrode and the internal electrode.

2. The fluid quality sensor for measuring mixture fluid according to claim 1, wherein the internal electrode has two ends extending along the second and third passages respectively, and cross-sectional areas of the second passage and the third passage are equal to that of the first passage.

3. The fluid quality sensor for measuring mixture fluid according to claim 2, wherein both of the two ends of the internal electrode are cone-shaped, and the second and third passages of the intake and outlet parts are tapered along the cone-shapes of the two ends of the internal electrode respectively.

4. The fluid quality sensor for measuring mixture fluid on according to claim 3, wherein an angle of the cone shape of each of the two ends of the internal electrode ranges from 10° to 60°.

5. The fluid quality sensor for measuring mixture fluid according to claim 1, wherein at least two points on an outer surface of the internal electrode are attached to the casing by the supporting members.

6. The fluid quality sensor for measuring mixture fluid according to claim 1, wherein the second members are engaged with the intake or outlet part in the axial direction, thereby preventing the external electrode, each of the first members and each of the second members from moving in the axial direction.

7. The fluid quality sensor for measuring mixture fluid according to claim 1, wherein a temperature sensor is connected to the external electrode.

8. The fluid quality sensor for measuring mixture fluid according to claim 1, wherein the pair of the second members are engaged with the first and second ends of the internal electrode, respectively, each of the second members being engaged with one of the first and second ends via four supporting members, thereby fixing the internal electrode relative to the tubular casing.

9. The fluid quality sensor for measuring mixture fluid according to claim 1, wherein the at least one supporting member is engaged with the surface of the at least one hole of each of the second members on one side of the supporting member and engaged with the outer surface of the internal electrode on an opposing side of the supporting member, thereby restricting the internal electrode from moving in the radial direction relative to the tubular casing.

10. The fluid quality sensor for measuring mixture fluid according to claim 1, wherein the internal electrode is connected to the tubular casing via the pair of the second members and the supporting members that support the respective second members.

11. The fluid quality sensor for measuring mixture fluid according to claim 1, wherein each of the supporting members is sandwiched between the respective second member and the internal electrode.

* * * * *